US011634782B2

(12) United States Patent
Stephens (10) Patent No.: US 11,634,782 B2
(45) Date of Patent: Apr. 25, 2023

(54) QUANTIFICATION OF MICROORGANISMS IN SAMPLES AND METHODS OF DETERMINING QUANTIFICATION CONDITIONS THEREOF

(71) Applicant: Hygiena, LLC, Camarillo, CA (US)

(72) Inventor: Tyler Stephens, Marion, TX (US)

(73) Assignee: HYGIENA, LLC, Camarillo, CA (US)

( * ) Notice: Subject to any disclaimer, the term of this patent is extended or adjusted under 35 U.S.C. 154(b) by 867 days.

(21) Appl. No.: 16/549,059

(22) Filed: Aug. 23, 2019

(65) Prior Publication Data

US 2020/0299752 A1  Sep. 24, 2020

Related U.S. Application Data

(60) Provisional application No. 62/821,051, filed on Mar. 20, 2019.

(51) Int. Cl.
| | | |
|---|---|---|
| *C12Q 1/689* | (2018.01) | |
| *C12Q 1/686* | (2018.01) | |
| *C07K 14/255* | (2006.01) | |
| *C12Q 1/10* | (2006.01) | |

(52) U.S. Cl.
CPC ............ *C12Q 1/689* (2013.01); *C07K 14/255* (2013.01); *C12Q 1/10* (2013.01); *C12Q 1/686* (2013.01); *C12Q 2561/113* (2013.01)

(58) Field of Classification Search
CPC .......... C12Q 1/689; C12Q 1/10; C12Q 1/686; C12Q 2561/113; C12Q 1/6851; C07K 14/255
See application file for complete search history.

(56) References Cited

U.S. PATENT DOCUMENTS

| | | |
|---|---|---|
| 5,210,015 A | 5/1993 | Gelfand et al. |
| 5,487,972 A | 1/1996 | Gelfand et al. |
| 5,538,848 A | 7/1996 | Livak et al. |
| 5,804,375 A | 9/1998 | Gelfand et al. |
| 5,994,056 A | 11/1999 | Higuchi |
| 6,171,785 B1 | 1/2001 | Higuchi |
| 6,312,930 B1 | 11/2001 | Tice, Jr. et al. |
| 6,326,145 B1 | 12/2001 | Whitcombe et al. |
| 6,483,303 B2 | 11/2002 | Simmonds et al. |
| 6,597,176 B2 | 7/2003 | Simmonds et al. |
| 6,607,922 B2 | 8/2003 | LaBorde |
| 7,323,139 B2 | 1/2008 | LaBorde et al. |

FOREIGN PATENT DOCUMENTS

| | | |
|---|---|---|
| WO | 97/11197 | 3/1997 |
| WO | 00/66777 | 11/2000 |

OTHER PUBLICATIONS

Hygiena.com, (https://cdn.brandfolder.io/KA71VJV5/at/3twc3r4mg4xs24k3qtc7qtbf/BAX-SalQuant-Ceca-Samples.pdf, pp. 1-4, indexed by Google, Dec. (Year: 2017).*
Frausto et al (Food Sci. Technol, Campinas, 33(3): 475-478, Jul.-Sep. (Year: 2013).*
Easter, M.C., et al., "Rapid and Automated Detection of *Salmonella* by Electrical Measurements", Journal of Hygene, 1985, vol. 94, pp. 245-262.
Sutton, Scott, "The Most Probable Number Method and Its Uses in Enumeration, Qualification, and Validation", Journal of Validation Technology, Summer 2010, vol. 16, No. 3, pp. 35-38.

* cited by examiner

*Primary Examiner* — Cynthia B Wilder
(74) *Attorney, Agent, or Firm* — McCarter & English, LLP (57) ABSTRACT

This disclosure relates to methods of determining quantification conditions for a microorganism and methods of quantifying microorganism concentration in a sample.

27 Claims, 2 Drawing Sheets

QUANTIFICATION OF MICROORGANISMS IN SAMPLES AND METHODS OF DETERMINING QUANTIFICATION CONDITIONS THEREOF

CROSS-REFERENCE TO RELATED APPLICATIONS

This application claims priority to U.S. Provisional Application No. 62/821,051, filed on Mar. 20, 2019, the contents of which are incorporated herein by reference in their entirety.

FIELD

The field relates to methods of quantitatively detecting microorganisms in samples.

BACKGROUND

Numerous diagnostic methods are available for detection and identification of microorganisms in any given samples obtained throughout the food production chain. Microorganisms can contaminate food or food animals during production, processing, and preparation.

Real-time quantification of microorganisms in real world samples is applicable to the food industry. However, current methods of enumeration take two to five days and are not very accurate (i.e., through use of Most Probable Numbers (MPN) and conventional plating). The MPN method estimates microorganism concentration in a sample through replicate liquid broth growth in 10-fold dilutions (Sutton, J. Valid. Technol. 16(3):35-38 (2010)), but the MPN method is a statistical probability with broad, overlapping ranges of microorganism numbers. It therefore has limited accuracy and precision.

Additionally, the MPN method requires long overnight enrichment periods in non-selective media to recover stressed cells. Use of selective media, however, slows cell growth rate thereby increasing enrichment to more than 24 hours, resulting in even longer microorganism detection times (though still having significant microorganism/sample accuracy problems). Sample sizes in the MPN method are also limited (e.g. to about 25 g to about 100 g), with a large sample to media ratio (approximately 1:10).

Currently, the food industry cannot provide adequate resolution into process interventions with qualitative prevalence results. Moreover, there is a high demand for quantification of microorganisms across several segments of the food industry to improve overall food safety.

SUMMARY

One aspect is for a method of determining quantification conditions for a microorganism in a sample comprising:
  (a) inoculating a plurality of samples from a sample lot with logarithmic serial dilutions of a microorganism in a quantification medium;
  (b) incubating the plurality of samples at one or more temperatures for a time period sufficient to detect the microorganism in the plurality of samples by a detection assay;
  (c) removing aliquots of the plurality of samples at a plurality of time points and at one or more temperatures of the incubation;
  (d) detecting a target nucleic acid sequence of the microorganism in each aliquot by the detection assay; and
  (e) determining a detection value at each time point and inoculation level to produce a linear best fit curve for the microorganism in the sample lot.

Another aspect is for a method of quantifying microorganism concentration in a sample comprising:
  (a) collecting a test sample from a test sample lot;
  (b) incubating the test sample (i) in a quantification medium (ii) for a pre-determined quantification time, (iii) at a pre-determined dilution ratio, and (iv) at a pre-determined temperature, wherein (i)-(iv) correlate to a pre-determined linear best fit curve for the microorganism from the test sample lot;
  (c) detecting, if present, a target nucleic acid sequence of the microorganism in the test sample by a detection assay; and
  (d) comparing the results of the detection assay with the pre-determined linear best fit curve to quantify an amount of microorganism in the test sample.

An additional aspect is for a method of quantifying microorganism concentration in a sample comprising:
  (a) inoculating a plurality of samples from a sample lot with logarithmic serial dilutions of a microorganism in a quantification medium;
  (b) incubating the plurality of samples in the quantification medium at one or more temperatures for a time period sufficient to detect the microorganism in the plurality of samples by a detection assay;
  (c) removing aliquots of the plurality of samples at a plurality of time points of the incubation;
  (d) detecting a target nucleic acid sequence of the microorganism in each aliquots by the detection assay;
  (e) determining a detection value at each time point and inoculation level to produce a linear best fit curve for the microorganism in the sample lot;
  (f) collecting a test sample from a test sample lot, wherein the test sample is of the same type as the sample lot;
  (g) incubating the test sample in the quantification medium (i) for a pre-determined quantification time, (ii) at a pre-determined dilution ratio, and (iii) at a pre-determined temperature, wherein (i)-(iii) correlate to the linear best fit curve for the microorganism in the sample lot;
  (h) detecting, if present, a test target nucleic acid sequence of the microorganism in the test sample by the detection assay; and
  (i) comparing the results of the detection assay of step (h) with the linear best fit curve to quantify an amount of microorganism in the test sample.

Other objects and advantages will become apparent to those skilled in the art upon reference to the detailed description that hereinafter follows.

DETAILED DESCRIPTION

Applicants specifically incorporate the entire contents of all cited references in this disclosure. Further, when an amount, concentration, or other value or parameter is given as either a range or a list of upper values and lower values, this is to be understood as specifically disclosing all ranges formed from any pair of any upper range limit or value and any lower range limit or value, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

Definitions

In this disclosure, a number of terms and abbreviations are used. The following definitions are provided.

As used herein, the term "about" or "approximately" means within 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%, or less of a given value or range.

The term "comprising" is intended to include embodiments encompassed by the terms "consisting essentially of" and "consisting of". Similarly, the term "consisting essentially of" is intended to include embodiments encompassed by the term "consisting of".

The term "detection value" refers to a signal (e.g., fluorescence, radioactivity, chemiluminesence, color, and the like) related to the quantity of a substance in a sample. Substances for detection include, but are not limited to, nucleic acids, antibodies, small molecules, and the like. Exemplary detection values include, but are not limited to, cycle threshold values, relative light units, signal to cutoff values, and optical densities.

"Polymerase chain reaction" is abbreviated PCR.

The terms "polynucleotide", "polynucleotide sequence", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide may also consist of nucleotide sequences joined at the 3' end of one nucleotide sequence to the 5' end of another nucleotide sequence by a linker such as a 3 or 6 carbon (propanediol or hexandiol, respectively) moiety, or a linker arm of either 3 or 6 polyethylene glycol subunits (triethylene glycol or hexaethylene glycol, respectively). Any suitable linkers or spacers that are known in the art will work for this application. A polynucleotide in the form of a polymer of DNA may be comprised of one or more strands of cDNA, genomic DNA, synthetic DNA, or mixtures thereof.

"Sample" means a small part or small quantity isolated from a subject (or a "sample lot") for analysis. In some embodiments, a sample lot is a food sample, or in some embodiments a food matrix. A food matrix can be, e.g., ground beef, beef trim, turkey carcass swabs, pork carcass swabs, beef carcass swabs, cattle hide swabs, fecal grab samples from cattle, ceca from turkey and chicken, and/or lymph from cattle, powders, spices, and/or pet food.

Standard recombinant DNA and molecular cloning techniques used here are well known in the art and are described by, e.g., Sambrook et al. (supra); and by Ausubel, F. M. et al., *Current Protocols in Molecular Biology*, published by Greene Publishing Assoc. and Wiley-Interscience (1987).

Methods

Applicants have solved the problem by determining that enrichment parameters (e.g., media type, sample to media dilution ratio, enrichment temperature, time) unique to each food/sample type and their respective processing environments must be developed to ensure accuracy of the quantification. After establishment of enrichment parameters, linear best fit curve generation through inoculation studies (e.g., ≥4 inoculation levels within the enumerable range of interest; e.g., ≥3 biological reps per inoculation level; e.g., ≥3 technical reps per biological sample) is required to provide the linear equation necessary for enumeration of microorganisms. Utilizing the linear equation, users can process samples in real time to quantify the current load of microorganism contamination at various processing points.

Applicants' methods use detection assays with a shortened enrichment time to statistically estimate pre-enrichment CFU/g, /mL, or /sample. A linear best fit curve is generated on a per food/sample type basis and the resulting equation is used to enumerate microorganisms throughout the food process.

Some embodiments are directed to methods of determining quantification conditions for a microorganism in a sample to establish a best fit curve for detecting the microorganism in a sample. Such methods can comprise, in some embodiments: (a) inoculating a plurality of samples from a sample lot with logarithmic serial dilutions of a microorganism in a quantification medium; (b) incubating the plurality of samples at one or more temperatures for a time period sufficient to detect the microorganism in the plurality of samples by a detection assay; (c) removing aliquots of the plurality of samples at a plurality of time points and at one or more temperatures of the incubation; (d) detecting a target nucleic acid sequence of the microorganism in each aliquot by the detection assay; and (e) determining a detection value at each time point and inoculation level to produce a linear best fit curve for the microorganism in the sample lot.

Generally in the present methods use of the smallest ratio of sample to medium will produce the shortest time to result. Thus, in some embodiments, the ratio of sample to medium is, e.g., about 1:0.5 or less, about 1:0.6, about 1:0.7, about 1:0.8, about 1:0.9, about 1:1, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, about 1:5, about 1:5.5, about 1:6, about 1:6.5, about 1:7, about 1:7.5, about 1:8, about 1:8.5, about 1:9, about 1:9.5, about 1:10, about 1:15, about 1:20, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, about 1:100 or more.

For the inoculation, a plurality of samples from a sample lot are diluted with logarithmic serial dilutions of a microorganism(s) in a quantification medium. The number of samples from the sample lot are determined by the number of logarithmic serial dilutions desired to produce a linear best fit curve for the microorganism(s) in the sample lot to be tested. The logarithmic serial dilutions can start a low dilution of about 0.1 or less, about 0.2, about 0.3, about 0.4, about 0.5, about 0.6, about 0.7, about 0.8, about 0.9, about 1.0, about 1.1, about 1.2, about 1.3, about 1.4, about 1.5, about 10, about 20, about 30, about 40, about 50, about 60, about 70, about 80, about 90, about 100, about 150, about 200, about 250, about 300, about 400, about 500, about 600, about 700, about 800, about 900, about 1000 or more CFU/mL. The number of logarithmic serial dilutions is not limited, and variations of logarithmic serial dilutions can be utilized (e.g., inoculations at 0, 0.5, 1, 1.5, 2, 2.5, 3, 3.5, 4, 4.5, 5, 5.5, 6, 6.5, 7, 7.5, 8, 8.5, 9, 9.5, 10 or more $\log_{10}$ dilutions, or e.g. inoculations at 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 or more $\log_{10}$ dilutions).

In some embodiments, each logarithmic serial dilution is replicated at least one time. Thus, in some embodiments, the method comprises 2, 3, 4, 5, 6, 7, 8, 9, 10, or more replications of each of the plurality of samples at logarithmic increments over a range of interest.

In some embodiments of the methods disclosed herein, the microorganism is a species of one or more of the following: *Acetobacter, Acetobacterium, Acholeplasma, Achromatium, Acidaminococcus, Acinetobacter, Actinobacillus, Actinomadura, Actinomyces, Actinoplanes, Actinopolyspora, Actinopycnidium, Actinosporangium, Actinosynnema, Aegyptianella, Aerococcus, Aeromonas, Agrobacterium, Agromyces, Alcaligenes, Alteromonas, Alysiella, Amoebobacter, Amorphosporangium, Ampullariella, Anaerobiospirillum, Anaeroplasma, Anaerovibrio, Anaplasma, Ancalochloris, Ancalomicrobium, Aquaspirillum, Arachnia, Archangium, Arthrobacter, Asticcacaulis, Azomonas, Azospirillum, Azotobacter, Bacillus, Bacterionema, Bacteroides, Bactoderma, Bartonella, Bdellovibrio, Beggiatoa, Beijerinckia, Beneckea, Bifidobacterium, Blastobacter, Blastococcus, Blattabacterium, Bordetella, Borrelia, Branhamella, Brevibacterium, Brochothrix, Brucella, Butyrivibrio, Calymmatobacterium, Campylobacter, Capsularis, Cardiobacterium, Caryophanon, Caseobacter, Caulobacter, Cellulomonas, Chainia, Chlamydia, Chlorobium, Chloroflexus, Chloronema, Chondromyces, Chromatium, Chromobacterium, Citrobacter, Clostridium, Coprococcus, Corynebacterium, Cowdria, Coxiella, Crenothrix, Cristispira, Curtobacterium, Cystobacter, Cytophaga, Dactylosporangium, Dermatophilus, Derxia, Desulfomonas, Desulfotomaculum, Desulfovibrio, Desulfuromonas, Ectothiorhodospira, Edwardsiella, Ehrlichia, Elytrosporangium, Enterobacter, Eperythrozoon, Erwinia, Erysipelothrix, Escherichia, Eubacterium, Excellospora, Flavobacterium, Flectobacillus, Flexibacter, Flexithrix, Francisella, Frankia, Fusobacterium, Gallionella, Gemella, Gemmiger, Geodermatophilus, Gluconobacter, Haemobartonella, Haemophilus, Hafnia, Haliscomenobacter, Halobacterium, Halococcus, Herpetosiphon, Hyphomicrobium, Janthinobacterium, Kineosporia, Kingella, Kitasatoa, Klebsiella, Kurthia, Lachnospira, Lactobacillus, Lamprocystis, Lampropedia, Legionella, Leptospira, Leptothrix, Leptotrichia, Leuconostoc, Leucothrix, Levinea, Listeria, Lucibacterium, Lysobacter, Macromonas, Megasphaera, Melittangium, Meniscus, Methanobacterium, Methanococcus, Methanosarcina, Methanospirillum, Methylobacillus, Methylobacterium, Methylococcus, Microbacterium, Microbispora, Micrococcus, Microcyclus, Microellobosporia, Micromonospora, Micropolyspora, Microscilla, Microtetraspora, Moraxella, Morganella, Mycobacterium, Mycoplana, Mycoplasma, Myxococcus, Nannocystis, Neisseria, Neorickettsia, Nevskia, Nitrobacter, Nitrococcus, Nitrosococcus, Nitrosolobus, Nitrosomonas, Nitrosospira, Nitrospina, Nocardia, Nocardioides, Nocardiopsis, Obesumbacterium, Oceanospirillum, Oerskovia, Oscillospira, Paracoccus, Pasteurella, Pasteuria, Pectinatus, Pectobacterium, Pediococcus, Pedomicrobium, Pelodictyon, Peptococcus, Peptostreptococcus, Photobacterium, Pilimelia, Planctomyces, Planobispora, Planococcus, Planomonospora, Plesiomonas, Polyangium, Promicromonospora, Propionibacterium, Prosthecochloris, Prosthecomicrobium, Proteus, Providencia, Pseudomonas, Pseudonocardia, Rhizobium, Rhodococcus, Rhodocyclus, Rhodomicrobium, Rhodopseudomonas, Rhodospirillum, Rickettsia, Rickettsiella, Rochalimaea, Rothia, Ruminococcus, Runella, Saccharomonospora, Saccharopolyspora, Salmonella, Saprospira, Sarcina, Selenomonas, Seliberia, Serpens, Serratia, Shigella, Simonsiella, Sphaerotilus, Spirillospora, Spirillum, Spirochaeta, Spiroplasma, Spirosoma, Sporichthya, Sporocytophaga, Sporolactobacillus, Sporosarcina, Staphylococcus, Stibiobacter, Stigmatella, Streptobacillus, Streptococcus, Streptomyces, Streptosporangium, Streptoverticillium, Succinimonas, Succinivibrio, Sulfolobus, Symbiotes, Thermoactinomyces, Thermomicrobium, Thermomonospora, Thermoplasma, Thermus, Thiobacillus, Thiocapsa, Thiocystis, Thiodictyon, Thiomicrospira, Thiopedia, Thioploca, Thiospira, Thiospirillum, Thiothrix, Thiovulum, Toxothrix, Treponema, Ureaplasma, Veillonella, Vibrio, Vitreoscilla, Wolbachia, Xanthobacter, Xanthomonas, Xenorhabdus, Yersinia, Zoogloea, Zymomonas*, and subspecies and serovars thereof.

In some embodiments of the methods disclosed herein, the microorganism is a species of one or more of the following: *Abstoma, Acutocapillitium, Agaricus, Allopsalliota, Arachnion, Attamyces, Barcheria, Battarrea, Battarreoides, Bovista, Bovistella, Calbovista, Calvatia, Chamaemyces, Chlamydopus, Chlorolepiota, Chlorophyllum, Clarkeinda, Clavogaster, Coccobotrys, Coniolepiota, Constricta, Coprinus, Crucispora, Cystoderma, Cystodermella, Cystolepiota, Discisеda, Echinoderma, Endolepiotula, Endoptychum, Eriocybe, Floccularia, Gasterellopsis, Gastropila, Glyptoderma, Gymnogaster, Gryophragmium, Heinemannomyces, Hiatulopsis, Holocotylon, Hymenagaricus, Hypogaea, Janauaria, Lepiota, Leucoagaricus, Leucocoprinus, Lycogalopsis, Lycoperdon, Lycoperdopsis, Macrolepiota, Melanophyllum, Metraria, Metrodia, Micropsalliota, Montagnea, Morganella, Mycenastrum, Mycocalia, Neosecotium, Panaeolopsis, Phaeopholiota, Phlebonema, Phyllogaster, Podaxis, Pseudoauricularia, Queletia, Rugosospora, Schinzinia, Secotium, Singerina, Smithiogaster, Smithiomyces, Termiticola, Tulostoma, Vascellum, Verrucospora, Xanthagaricus, Xerocoprinus, Brunneocorticium, Cheilophlebium, Cleistocybe, Cribrospora, Disporotrichum, Mesophelliopsis, Panaeolina, Panaeolus, Phelbophyllum, Plicatura, Plicaturopsis, Sedecula, Setchelliogaster, Trichocybe, Amanita, Catatrama, Limacella, Saproamanita, Agrogaster, Bolbitius, Conocybe, Cyphellopus, Cyttarophyllopsis, Galerella, Galeropsis, Gymnoglossum, Pholiotina, Pytchella, Rhodoarrhenia, Tubariella, Tubariopsis, Tympanella, Wielandomyces, Broomeia, Camarophyllopsis, Clavaria, Clavulinopsis, Hyphodontiella, Mucronella, Ramariopsis, Scytinopogon, Anamika, Cortinarius, Descolea, Descomyces, Hemistropharia, Mackintoshia, Nanstelocephala, Phaecollybia, Protoglossum, Pyrrhoglossum, Quadrispora, Stephanopus, Asterocyphella, Campanophyllum, Catilla, Cheimonophyllum, Chondrostereum, Cunninghammyces, Cyphella, Gloeocorticium, Gloeostereum, Granulobasidium, Hyphoradulum, Incrustocalyptella, Phaeoporotheleum, Seticyphella, Sphaerobasidioscypha, Thujacorticium, Clitopilus, Entoloma, Rhodocybella, Fistulina, Porodisculus, Pseudofistulina, Gigasperma, Hemigaster, Hydnangium, Laccaria, Maccagnia, Acantholichen, Ampulloclitocybe, Arrhenia, Camarophyllus, Cantharocybe, Chromosera, Chrysomphalina, Eonema, Gliophorus, Haasiella, Humidicutis, Hygrocybe, Hygrophorus,*

*Lichenomphalia, Pseudoarmillariella, Semiomphalina, Auritella, Chromocyphella, Episphaeria, Flammulaster, Inocybe, Phaeomarasmius, Phaeomyces, Phaeosolenia, Tubaria, Tubariomyces, Limnoperdon, Asterophora, Blastosporella, Calocybe, Hypsizgus, Lyophyllopsis, Lyophyllum, Ossicaulis, Tephrocybe, Termitomyces, Tricholomella, Decapitatus, Favolaschia, Flabellimycena, Hemimycena, Mycena, Panellus, Protomycena, Resinomycena, Roridomyces, Tectella, Xeromphalina, Flagelloscypha, Halocyphina, Lachnella, Merismodes, Nia, Woldmaria, Dictyocephalos, Phellorinia, Cribbea, Agaricochaete, Antromycopsis, Hohenbuehelia, Nematoctonus, Pleurotus, Chamaeota, Pluteus, Volvariella, Volvopluteus, Coprinellus, Coprinopsis, Cystoagaricus, Gasteroagaricoides, Lacrymaria, Palaeocybe, Parasola, Macrometrula, Mythicomyces, Psathyrella, Actiniceps, Adustomyces, Allantula, Aphanobasidium, Chaetotyphula, Coronicium, Merilicium, Parapterulicium, Pyllotopsis, Pterula, Pterulicium, Radulomyces, Auriculariopsis, Schizophyllum, Lutypha, Macrotyphula, Pistillaria, Pistillina, Sclerotium, Typhula, Acallomyces, Acompsomyces Acrogynomyces, Amorphomyces, Amphimyces, Apatelomyces, Apatomyces, Aphanandromyces, Aporomyces, Arthrorhynchus, Asaphomyces, Autophagomyces, Balazusia, Benjaminiomyces, Blasticomyces, Botryandromyces, Camptomyces, Cantharomyces, Capillistichus, Carpophoromyces, Chaetarthriomyces, Chaetomyces, Chitonomyces, Clematomyces, Clonophoromyces, Columnomyces, Compsomyces, Coreomyces, Corethromyces, Corylophomyces, Cryptandromyces, Cucujomyces, Cupulomyces, Dermapteromyces, Diandromyces, Diaphoromyces, Diclonomyces, Dimeromyces, Dimorphomyces, Dioicomyces, Diphymyces, Diplomyces, Diplopodomyces, Dipodomyces, Distolomyces, Dixomyces, Ecteinomyces, Enarthromyces, Eucantharomyces, Euhaplomyces, Eumisgomyces, Eumonoicomyces, Euphoriomyces, Fanniomyces, Filariomyces, Gloeandromyces, Haplomyces, Hesperomyces, Histeridomyces, Homaromyces, Hydraeomyces, Hydrophilomyces, Idiomyces, Ilyomyces, Ilytheomyces, Kainomyces, Kleidiomyces, Kruphaiomyces, Kyphomyces, Laboulbenia, Limnaiomyces, Majewskia, Meionomyces, Microsomyces, Mimeomyces, Misgomyces, Monandromyces, Monoicomyces, Nanomyces, Neohaplomyces, Nycteromyces, Ormomyces, Osoriomyces, Parvomyces, Peyerimhoffiella, Peyritschiella, Phalacrichomyces, Phaulomyces, Picardella, Polyandromyces, Polyascomyces, Porophoromyces, Prolixandromyces, Pselaphidomyces, Rhachomyces, Rhipidiomyces, Rhizomyces, Rhizopodomyces, Rickia, Rossiomyces, Sandersoniomyces, Scalenomyces, Scaphidiomyces, Scelophoromyces, Scepastocarpus, Siemaszkoa, Smeringomyces, Sphaleromyces, Stemmatomyces, Stichomyces, Stigmatomyces, Sugiyamaemyces, Symplectromyces, Sympodomyces, Synandromyces, Tavaresiella, Teratomyces, Tetrandromyces, Trenomyces, Triainomyces, Triceromyces, Trochoideomyces, Troglomyces, Zeugandromyces, Zodiomyces, Amyloflagellula, Anastrophella, Anthracophyllum, Aphyllotus, Baeospora, Calathella, Calyptella, Campanella, Caripia, Cephaloscypha, Chaetocalathus, Clitoybula, Connopus, Crinipellis, Cymatella, Cymatellopsis, Deigloria, Epicnaphus, Fissolimbus, Gerronema, Glabrocyphella, Gymnopus, Henningsomyces, Hispidocalyptella, Hydropus, Hymenogloea, Lactocollybia, Lecanocybe, Lentinula, Macrocystidia, Manuripia, Marasmiellus, Marasmius, Megacollybia, Metulocyphella, Moniliophthora, Mycetinis, Neocampanella, Neonothopanus, Nochascypha, Nothopanus, Omphalotus, Palaeocephala, Phaeodepas, Pleurocybella, Pseudotyphula, Rectipilus, Rhodocollybia, Skepperiella, Stipitocyphella, Stromatocyphella, Tetrapyrgos, Trogia,*

*Abelspora, Agglomerata, Agmasoma, Alfvenia, Alloglugea, Amazonspora, Amblyospora, Ameson, Amphiacantha, Amphiamblys, Anncallia, Antonospora, Aurospora, Bacillidium, Baculea, Berwaldia, Binucleospora, Bohuslavia, Burenella, Burkea, Brachiola, Bryonosema, Buxtehudea, Campanulospora, Canningia, Caudospora, Chapmanium, Chytridiopsis, Ciliatosporidium, Coccospora, Cougourdella, Cryptosporina, Cucumispora, Culicospora, Culicosporella, Cristulospora, Cylindrospora, Cystosporogenes, Desportesia, Dictyocoela, Duboscqia, Edhazardia, Encephalitozoon, Endoreticulatus, Enterocytozoon, Episeptum, Evlachovaia, Fibrillanosema, Flabelliforma, Geusia, Glugea, Glugoides, Golbergia, Gurleya, Gurleyides, Hamiltosporidium, Hazardia, Helmichia, Hessea, Heterosporis, Hirsutosporos, Holobispora, Hrabeyia, Hyalinocysta, Ichthyosporidium, Inodosporus, Intexta, Intrapredatorus, Janacekia, Jirovecia, Jiroveciana, Johenrea, Kabatana, Kinorhyncospora, Lanatospora, Larssonia, Larssoniella, Liebermannia, Loma, Marssoniella, Merocinta, Metchnikovella, Microfilum, Microgemma, Microsporidium, Mrasekia, Myosporidium, Nadelspora, Napamichum, Nelliemelba, Neonosemoides, Neoperezia, Nolleria, Norlevinea, Nosema, Nosemoides, Nucleospora, Nudispora, Octospora, Octotetraspora, Oligosporidium, Ordospora, Ormieresia, Orthosomella, Ovavesicula, Ovipleistophora, Paranosema, Parapleistophora, Parastempellia, Parathelohania, Pegmatheca, Perezia, Pernicivesicula, Pilosporella, Pleistophora, Pleistosporidium, Polydispyrenia, Pseudoloma, Pseudonosema, Pseudopleistophora, Pulicispora, Pyrotheca, Rectispora, Resiomera, Ringueletium, Schroedera, Scipionospora, Semenovaia, Senoma, Simuliospora, Spherospora, Spraguea, Steinhausia, Stempellia, Striatospora, Systenostrema, Tabanispora, Tardivesicula, Telomyxa, Tetramicra, Thelohania, Toxoglugea, Toxospora, Trachipleistophora, Trichoduboscqia, Trichonosema, Trichoctospora, Trichotuzetia, Tricornia, Tubulinosema, Tuzetia, Unikaryon, Vittaforma, Vairimorpha, Vavraia, Visvesvaria, Vittaforma, Weiseria, Wittmannia, Ahtiana, Almbomia, Alectoria, Allantoparmelia, Allocetraria, Anzia, Arctocetraria, Arctoparmelia, Asahinea, Brodoa, Bryocaulon, Bryoria, Bulborrhizina, Bulbothrix, Canoparmelia, Cavemularia, Cetraria, Cetrariastrum, Cetrariella, Cetrariopsis, Cetrelia, Coelopogon, Comicularia, Coronoplectrum, Dactylina, Davidgallowaya, Esslingeriana, Evernia, Everniastrum, Everniopsis, Flavocetraria, Flavoparmelia, Flavopunctelia, Himantormia, Hypogymnia, Hypotrachyna, Imshaugia, Kaemefeltia, Karoowia, Letharia, Lethariella, Masonhalea, Melanelia, Melanelixia, Melanohalea, Menegazzia, Myelochroa, Namakwa, Neopsoromopsis, Nephromopsis, Nipponoparmelia, Nodobryoria, Omphalodiella, Omphalodium, Omphalora, Oropogon, Pannoparmelia, Parmelaria, Parmelia, Parmelina, Parmelinella, Parmelinopsis, Parmeliopsis, Parmotrema, Parmotremopsis, Phacopsis, Placoparmelia, Platismatia, Pleurosticta, Protoparmelia, Protousnea, Pseudephebe, Pseudevernia, Pseudoparmelia, Psiloparmelia, Psoromella, Punctelia, Relicina, Relicinopsis, Sulcaria, Tuckermanella, Tuckermannopsis, Usnea, Usnocetraria, Vulpicida, Xanthomaculina, Xanthoparmelia, Amparoina, Arthromyces, Arthrosporella, Asproinocybe, Austroclitocybe, Austroomphaliaster, Callistodermatium, Callistosporium, Cantharellopsis, Catathelasma, Caulorhiza, Cellypha, Clavomphalia, Clitocybe, Collybia, Conchomyces, Corneriella, Cynema, Cyphellocalathus, Delicatula, Dendrocollybia, Dennisiomyces, Dermoloma, Fayodia, Gamundia, Hygroaster, Infundibulicybe, Lepista, Lepistella, Leucocortinarius, Leucoinocybe, Leucopaxillus, Leucopholiota, Lule-* sia, Macrocybe, Melanoleuca, Melanomphalia, Musumecia, Mycenella, Mycoalvimia, Myxomphalia, Neoclitocybe, Nothoclavulina, Omphaliaster, Omphalina, Paralepista, Paralepistopsis, Peglerochaete, Pegleromyces, Phaeomycena, Phyllotopsis, Physocystidium, Pleurella, Pleurocollybia, Pogonoloma, Porpoloma, Pseudobaeospora, Pseudoclitocybe, Pseudohygrophorus, Pseudolaccaria, Pseudolasiobolus, Pseudoomphalina, Pseudotricholoma, Resupinatus, Rimbachia, Ripartites, Squamanita, Stanglomyces, Tilachlidiopsis, Tricholoma, Tricholomopsis, Tricholosporum, and subspecies thereof.

In order to determine the optimal temperature for establishing a linear best fit curve for the microorganism in a sample lot, the plurality of samples are incubated at one or more temperatures for a time period sufficient to detect the microorganism in the plurality of samples by a detection assay. The temperature for optimal detection of the microorganism can be about 32.0 or less, about 32.1 about 32.2, about 32.3, about 32.4, about 32.5, about 32.6, about 32.7, about 32.8, about 32.9, about 33.0, about 33.1 about 33.2, about 33.3, about 33.4, about 33.5, about 33.6, about 33.7, about 33.8, about 33.9, about 34.0, about 34.1 about 34.2, about 34.3, about 34.4, about 34.5, about 34.6, about 34.7, about 34.8, about 34.9, about 35.0, about 35.1 about 35.2, about 35.3, about 35.4, about 35.5, about 35.6, about 35.7, about 35.8, about 35.9, about 36.0, about 36.1 about 36.2, about 36.3, about 36.4, about 36.5, about 36.6, about 36.7, about 36.8, about 36.9, about 37.0, about 37.1 about 37.2, about 37.3, about 37.4, about 37.5, about 37.6, about 37.7, about 37.8, about 37.9, about 38.0, about 38.1 about 38.2, about 38.3, about 38.4, about 38.5, about 38.6, about 38.7, about 38.8, about 38.9, about 39.0, about 39.1 about 39.2, about 39.3, about 39.4, about 39.5, about 39.6, about 39.7, about 39.8, about 39.9, about 40.0, about 40.1 about 40.2, about 40.3, about 40.4, about 40.5, about 40.6, about 40.7, about 40.8, about 40.9, about 41.0, about 41.1 about 41.2, about 41.3, about 41.4, about 41.5, about 41.6, about 41.7, about 41.8, about 41.9, about 42.0, about 42.1 about 42.2, about 42.3, about 42.4, about 42.5, about 42.6, about 42.7, about 42.8, about 42.9, about 43.0, about 43.1 about 43.2, about 43.3, about 43.4, about 43.5, about 43.6, about 43.7, about 43.8, about 43.9, about 44.0, about 44.1 about 44.2, about 44.3, about 44.4, about 44.5, about 44.6, about 44.7, about 44.8, about 44.9, about 45.0, about 45.1 about 45.2, about 45.3, about 45.4, about 45.5, about 45.6, about 45.7, about 45.8, about 45.9, about 46.0, about 46.1 about 46.2, about 46.3, about 46.4, about 46.5, about 46.6, about 46.7, about 46.8, about 46.9, about 47.0, about 47.1 about 47.2, about 47.3, about 47.4, about 47.5, about 47.6, about 47.7, about 47.8, about 47.9, about 48.0 or more ° C., and can be determined based on assay need, microorganism tolerance, and/or user preference. In some embodiments, a temperature range can be used, e.g., 32-48° C., 33-48° C., 34-48° C., 35-48° C., 36-48° C., 37-48° C., 38-48° C., 39-48° C., 40-48° C., 41-48° C., 42-48° C., 43-48° C., 44-48° C., 45-48° C., 46-48° C., 47-48° C., 32-47° C., 33-47° C., 34-47° C., 35-47° C., 36-47° C., 37-47° C., 38-47° C., 39-47° C., 40-47° C., 41-47° C., 42-47° C., 43-47° C., 44-47° C., 45-47° C., 46-47° C., 32-46° C., 33-46° C., 34-46° C., 35-46° C., 36-46° C., 37-46° C., 38-46° C., 39-46° C., 40-46° C., 41-46° C., 42-46° C., 43-46° C., 44-46° C., 45-46° C., 32-45° C., 33-45° C., 34-45° C., 35-45° C., 36-45° C., 37-45° C., 38-45° C., 39-45° C., 40-45° C., 41-45° C., 42-45° C., 43-45° C., 44-45° C., 32-44° C., 33-44° C., 34-44° C., 35-44° C., 36-44° C., 37-44° C., 38-44° C., 39-44° C., 40-44° C., 41-44° C., 42-44° C., 43-44° C., 32-43° C., 33-43° C., 34-43° C., 35-43° C., 36-43° C., 37-43° C., 38-43° C., 39-43° C., 40-43° C., 41-43° C., 42-43° C., 32-42° C., 33-42° C., 34-42° C., 35-42° C., 36-42° C., 37-42° C., 38-42° C., 39-42° C., 40-42° C., 41-42° C., 32-41° C., 33-41° C., 34-41° C., 35-41° C., 36-41° C., 37-41° C., 38-41° C., 39-41° C., 40-41° C., 32-40° C., 33-40° C., 34-40° C., 35-40° C., 36-40° C., 37-40° C., 38-40° C., 39-40° C., 32-39° C., 33-39° C., 34-39° C., 35-39° C., 36-39° C., 37-39° C., 38-39° C., 32-38° C., 33-38° C., 34-38° C., 35-38° C., 36-38° C., 37-38° C., 32-37° C., 33-37° C., 34-37° C., 35-37° C., 36-37° C., 32-36° C., 33-36° C., 34-36° C., 35-36° C., 32-35° C., 33-35° C., 34-35° C., 32-34° C., 33-34° C., or 32-33° C.

The optimal temperature determined through testing of one or more temperatures to establish a linear best fit curve can then be used in a method to quantify a microorganism in a test sample from a test sample lot.

In order to determine the optimal time of microorganism incubation in the quantification medium for establishing a linear best fit curve for the microorganism in a sample lot, the plurality of samples are incubated at one or more time periods sufficient to detect the microorganism in the plurality of samples by a detection assay. The time period for optimal detection of the microorganism can be about 10 hours or longer, or about 10, about 9.9, about 9.8, about 9.7, about 9.6, about 9.5, about 9.4, about 9.3, about 9.2, about 9.1, about 9.0, about 8.9, about 8.8, about 8.7, about 8.6, about 8.5, about 8.4, about 8.3, about 8.2, about 8.1 about 8.0, about 7.9, about 7.8, about 7.7, about 7.6, about 7.5, about 7.4, about 7.3, about 7.2, about 7.1, about 7.0, about 6.9, about 6.8, about 6.7, about 6.6, about 6.5, about 6.4, about 6.3, about 6.2, about 6.1, about 6.0, about 5.9, about 5.8, about 5.7, about 5.6, about 5.5, about 5.4, about 5.3, about 5.2, about 5.1, about 5.0, about 4.9, about 4.8, about 4.7, about 4.6, about 4.5, about 4.4, about 4.3, about 4.2, about 4.1, about 4.0, about 3.9, about 3.8, about 3.7, about 3.6, about 3.5, about 3.4, about 3.3, about 3.2, about 3.1, about 3.0, about 2.9, about 2.8, about 2.7, about 2.6, about 2.5, about 2.4, about 2.3, about 2.2, about 2.1, about 2.0 hours or less. In some embodiments, a target incubation time is selected (e.g., 4 hours) and then multiple incubation times are used around the target incubation time (e.g., if 4 hours is the target incubation time, then 2 and 6 hour time periods can also be used) to determine the linear best fit curve for the microorganism in the sample lot. The time periods can be shifted if necessary to determine the linear best fit curve.

The optimal time period determined through testing of one or more time periods to establish a linear best fit curve can then be used in a method to quantify a microorganism in a test sample from a test sample lot.

In some embodiments of methods to establish a linear best fit curve, more than one aliquot of the each of the plurality of samples can be removed from the incubation at each tested time point to provide further accuracy of microorganism(s) detection at each time point. For example, in some embodiments where more than one aliquot is removed for microorganism detection, 2, 3, 4, 5, 7, 8, 9, 10, or more aliquots can be removed for testing.

The act of testing a sample for a microorganism is a detection even if the microorganism is determined to be not present or below the level of sensitivity. Detection may be applied to any sample wherein the presence or absence of the microorganism is to be assessed. In some embodiments, and without limitation, the step of detecting a microorganism may comprise using PCR, real-time PCR, lectins, simple diffusion, lateral diffusion, immunological detection, lateral flow, or flow through methods to detect the presence of the microorganism. By way of illustration and not limitation, in particular embodiments possible detecting methods include or use the subject matter disclosed in any of U.S. Pat. Nos. 6,483,303; 6,597,176; 6,607,922; and 7,323,139, each of which is hereby incorporated by reference in its entirety. In some embodiments, microorganisms may be detected individually. In some embodiments, multiple microorganisms may be detected simultaneously. In some embodiments, microorganism detection may be by a detection assay such as multiplex PCR, multiplex ELISA, DNA microarray, protein microarray, or bead based assays such as a Luminex® assay. In some embodiments, Luminex® assays may use microspheres.

In some embodiments, primer-directed amplification products can be analyzed using various methods. "Homogenous detection" refers to a method for the detection of amplification products where no separation (such as by gel electrophoresis) of amplification products from template or primers is necessary. Homogeneous detection is typically accomplished by measuring the level of fluorescence of the reaction mixture during or immediately following amplification. In addition, heterogeneous detection methods, which involve separation of amplification products during or prior to detection, can be employed in the present methods.

Homogenous detection may be employed to carry out "real-time" primer-directed nucleic acid amplification and detection, using primer pairs of the instant disclosure (e.g., "real-time" PCR and "real-time" RT-PCR). Exemplary "real-time" methods are set forth in U.S. Pat. Nos. 6,171,785, 5,994,056, 6,326,145, 5,804,375, 5,538,848, 5,487,972, and 5,210,015, each of which is hereby incorporated by reference in its entirety.

In some embodiments, the "real-time" detection method is the 5'-exonuclease detection method, as set forth in U.S. Pat. Nos. 5,804,375, 5,538,848, 5,487,972, and 5,210,015, each of which is hereby incorporated by reference in its entirety. In the 5'-exonuclease detection assay, a modified probe is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are, in some embodiments, attached to the probe within a few nucleotides of one another, usually within 30, 29, 28, 27, 26, 25, 24, 23, 22, 21, 20, 19, 18, 17, 16, 15, 14, 13, 12, 11, 10, 9, 8, 7, or 6 nucleotides of one another. Typically, this separation is achieved by attaching one member of a reporter-quencher pair to the 5' end of the probe and the other member to a nucleotide about 30, 29, 28, 27, 26, 25, 24, 23, 22, 21, 20, 19, 18, 17, 16, 15, 14, 13, 12, 11, 10, 9, 8, 7, or 6 nucleotides away.

In some embodiments, amplification and detection is performed using labeled Taqman® probes. In some embodiments, a CAL Fluor 610 reporter is attached at the 5' terminus and a BHQ2 quencher attached at the 3' terminus.

Another "real-time" detection method is the Scorpion® probe assay as set forth in U.S. Pat. No. 6,326,145, which is hereby incorporated by reference in its entirety. In the Scorpion® probe assay, PCR amplification is performed using a Scorpion® probe (either unimolecular or bimolecular) as a primer-probe complex, the Scorpion® probe possessing an appropriate reporter-quencher pair to allow the detectable signal of the reporter to be quenched prior to elongation of the primer. Post-elongation, the quenching effect is eliminated, and the amount of signal present is quantitated. As the amount of amplification product increases, an equivalent increase in detectable signal will be observed, thus allowing the amount of amplification product present to be determined as a function of the amount of detectable signal measured. When more than one Scorpion® probe is employed in a Scorpion® probe assay, such as one directed to more than one DNA region of interest (such as, e.g., one probe directed to one target region and a second probe directed to a different target region), each probe can have a different detectable label (e.g., reporter-quencher pair) attached, thus allowing each probe to be detected independently of the other probes.

Another method of homogenous detection involves the use of DNA melting curve analysis, particularly with the BAX® System hardware and reagent tablets from Hygiena, LLC (Camarillo, Calif.). The details of the system are given in U.S. Pat. No. 6,312,930 and PCT Publication Nos. WO 97/11197 and WO 00/66777, each of which is hereby incorporated by reference in its entirety.

Melting curve analysis detects and quantifies double stranded nucleic acid molecule ("dsDNA" or "target") by monitoring the fluorescence of the target amplification product ("target amplicon") during each amplification cycle at selected time points.

As is well known to the skilled artisan, the two strands of a dsDNA separate or melt, when the temperature is higher than its melting temperature. Melting of a dsDNA molecule is a process, and under a given solution condition, melting starts at a temperature (designated $T_{MS}$ hereinafter), and completes at another temperature (designated $T_{ME}$ hereinafter). The familiar term, $T_m$, designates the temperature at which melting is 50% complete.

A typical PCR cycle involves a denaturing phase where the target dsDNA is melted, a primer annealing phase where the temperature optimal for the primers to bind to the now-single-stranded target, and a chain elongation phase (at a temperature $T_E$) where the temperature is optimal for DNA polymerase to function.

In a melt curve analysis, $T_{MS}$ should be higher than $T_E$, and $T_{ME}$ should be lower (often substantially lower) than the temperature at which the DNA polymerase is heat-inactivated. Melting characteristics are affected by the intrinsic properties of a given dsDNA molecule, such as deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship.

Examples of such intercalating dyes include, but are not limited to, SYBR® Green-I, ethidium bromide, propidium iodide, TOTO®-1 {Quinolinium, 1-1'-[1,3-propanediylbis[(dimethyliminio)-3,1-propanediyl]]bis[4-[(3-methyl-2(3H)-benzothiazolylidene) methyl]]-, tetraiodide}, and YoPro® {Quinolinium, 4-[(3-methyl-2(3H)-benzoxazolylidene)methyl]-1-[3-(trimethylammonio)-propyl]-,diiodide}. In some embodiments, a non-asymmetrical cyanide dye such as SYBR® Green-I, manufactured by ThermoFisher Scientific, is the intercalating dye.

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve.

It should be understood that the present methods could be operated using a combination of techniques, such as by having a Scorpion® probe directed to one target region and a Taqman® probe directed to a second target region. It should also be understood that the methods are not limited to the above described techniques. Rather, one skilled in the art would recognize that other techniques for detecting amplification as known in the art may also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher nucleic acid probe with the amplified target nucleic acid sequence, the reporter and quenchers become sufficiently distant from each other. As a result, the quenching is substantially abated causing an increase in the fluorescence emission detected.

In addition to homogenous detection methods, a variety of other heterogeneous detection methods are known in the art which can be employed in the present methods, including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant, it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the dsDNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (e.g., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

In some embodiments, the detection assay is a non-amplification based assay. Methods considered are, by way of non-limiting example, chromatography, mass spectrometry (and combinations thereof), enzymatic assays, electrophoresis and antibody-based assays, such as but not limited to EIA (Enzyme Immuno Assay), RIA (Radio Immuno Assay), Immunoblotting, ELISA (Enzyme Linked ImmunoSorbent Assay), CLIA (ChemiLuminescent Immuno Assay), CEDIA (Cloned Enzyme Donor Immunoassay), CMIA (Chemiluminescent Microparticle Immunoassay), MEIA (Microparticle Enzyme Immunoassay), FPIA (Fluorescence Polarization Immunoassay), GLORIA (Gold-Labeled, Optically read, Rapid Immunoassay), microarray analysis, fully-automated or robotic immunoassays and latex agglutination assays.

Contacting a sample with a capture reagent under conditions effective and for a period of time sufficient to allow the formation of immune complexes is generally a matter of adding the capture reagent to the sample and incubating the mixture for a period of time long enough for the antibodies to form immune complexes with the antigen presented. A target/antibody mixture can be detected by known means and methods, that is, detection of immune complex formation of target/antibody can be achieved through the application of numerous approaches. These methods are generally based upon the detection of a label or marker, such as any radioactive, fluorescent, biological, or enzymatic tags or labels of standard use in the art. In some embodiments, a secondary binding ligand such as a second antibody or a biotin/avidin (streptavidin) ligand binding arrangement as it is known in the art can be used.

In some embodiments, the detection method can comprise one or more of the following steps. In a first step, one or more aliquots from the incubated sample is contacted and incubated with a capture (or coat) reagent. Immobilization conventionally is accomplished by insolubilizing the capture reagent either before the assay procedure, as by adsorption to a water-insoluble matrix or surface or non-covalent or covalent coupling (e.g., using glutaraldehyde or carbodiimide cross-linking, with or without prior activation of the support with, e.g., nitric acid and a reducing agent, or afterward, e.g., by immunoprecipitation).

The solid phase used for immobilization may be any inert support or carrier that is essentially water insoluble and useful in immunometric assays, including supports in the form of, e.g. surfaces, particles, porous matrices, etc. Examples of commonly used supports include small sheets, Sephadex® (cross-linked dextran gel), polyvinyl chloride, plastic beads, and assay plates or test tubes manufactured from polyethylene, polypropylene, polystyrene, and the like including 96- or 384-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates are suitably employed for capture reagent immobilization. In some embodiments the capture reagent is coated on a microtiter plate, e.g., a multi-well microtiter plate that can be used to analyze several samples at one time, e.g. a microtest 96- or 384-well ELISA plate.

The solid phase can be coated with the capture reagent, which may be linked by a non-covalent or covalent interaction or physical linkage as desired. If covalent, the plate or other solid phase is incubated with a cross-linking agent together with the capture reagent under conditions well known in the art, e.g., such as for 1 hour at room temperature. Commonly used cross-linking agents for attaching the capture reagent to the solid phase substrate include, e.g., 1,1-bis(diazoacetyl)-2-phenylethane, glutaraldehyde, N-hydroxy-succinimide esters, homobifunctional imidoesters, and bifunctional maleimides. Derivatizing agents such as methyl-3-[(p-azidophenyl)-dithio]pro-pioimi-date yield photoactivatable intermediates capable of forming cross-links in the presence of light.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, and can be performed in advance of actual testing and stored under proper conditions for later use. After coating and blocking, the sample to be analyzed, appropriately diluted, is added to the immobilized phase. The final concentration of the capture reagent will normally be determined empirically to maximize the sensitivity of the assay over the range of interest. The conditions for incubation of sample and immobilized capture reagent are selected to maximize sensitivity of the assay and to minimize dissociation. In some embodiments, the incubation is accomplished at fairly constant temperatures, ranging from about 0° C. to about 40° C., in some embodiments, from about 20 to 37° C., or 20-40° C., 25-40° C., 30-40° C., 35-40° C., 25-37° C., 30-37° C., 35-37° C., 20-35° C., 25-35° C., 30-35° C., 20-30° C., 25-30° C., or 20-25° C. The time for incubation depends primarily on the temperature, being generally no greater than about 10, 9, 8, 7, 6, 5, 4, 3, 2, or 1 hours to avoid an insensitive assay. In some embodiments, the incubation time is from about 0.5 to 3 hours, 1 to 3 hours, 1.5 to 3 hours, 2 to 3 hours, 2.5 to 3 hours, 0.5 to 2.5 hours, 1 to 2.5 hours, 1.5 to 2.5 hours, 2 to 2.5 hours, 0.5 to 2 hours, 1 to 2 hours, 1.5 to 2 hours, 0.5 to 1.5 hours, 1 to 1.5 hours, or 0.5 to 1 hour to maximize binding.

The pH of the incubation buffer can be chosen to maintain a significant level of specific binding. Various buffers may be employed allowing for the specific binding of an antibody to an epitope and generally include aqueous buffer systems or aqueous solutions at physiologic pH and ionic strength. Such buffers can be, by way of non-limiting example, carbonate buffer, phosphate buffered saline, sodium phosphate buffer systems, Tris/HCl buffer, glycine buffer, or acetate buffer. The pH of the buffer can range between 5 and 10, e.g., pH 5, 5.5, 6, 6.5, 7, 7.5, 8, 8.5, 9, 9.5, or 10. Salt concentrations can be between 0 and 250 mmol/l using sodium chloride or an equivalent salt. Buffers may be supplemented with high salt concentrations up to 1 M to avoid unwanted interactions.

In a further step, which is optional, the sample can be separated (e.g., by washing) from the capture reagent to remove uncaptured molecules. The solution used for washing is generally a buffer with a pH determined using the considerations and buffers described above for the incubation step, with a pH range of about 6-9, e.g., pH 6, 6.5, 7, 7.5, 8, 8.5, or 9. The washing may be performed 1, 2, 3 or more times. The temperature of washing is generally from refrigerator to moderate temperatures, with a constant temperature maintained during the assay period, typically from about 0-40° C.

In a next step, the capture reagent is contacted with detectable antibodies, preferably at a temperature of about 20-40° C., in some embodiments, from about 20 to 37° C., or 20-40° C., 25-40° C., 30-40° C., 35-40° C., 25-37° C., 30-37° C., 35-37° C., 20-35° C., 25-35° C., 30-35° C., 20-30° C., 25-30° C., or 20-25° C., with the exact temperature and time for contacting the two being dependent primarily on the detection means employed.

This antibody is directly or indirectly detectable. The detectable antibody may be a polyclonal or monoclonal antibody. Also the detectable antibody can be directly detectable, and in some embodiments has a colorimetric label, in some embodiments has a fluorometric label, and in some embodiments has a radioactive label.

In some embodiments, to create a linear best fit curve for a non-molecular detection assay, a standard curve can be obtained by plotting the optical density (OD) or absorbance for each standard concentration against a target (e.g., protein) concentration. Using those results, a best-fit curve can be created, e.g., by regression analysis (using, e.g., ELISA or Luminex® assay) and the value of the sample of interest can be calculated using the portion of the standard curve that provides accurate (calculated value compared to actual value) and reproducible results. This can be constructed manually or automatically using plotting software. For manual calculation, OD or absorbance can be obtain from the readout or printout of, e.g., a microplate reader. Samples that have an OD or absorbance value that falls out of the range of the standard curve can be tested again after further dilution, and the concentration obtained from the standard curve after analysis of the results is then multiplied by the dilution factor.

By identifying the best enrichment parameters (e.g., time, temperature, medium, dilution ratio), it is possible to produce a linear best fit curve capable of providing an $R^2$ of at least about 0.85, 0.86, 0.87, 0.88, 0.89, 0.90, 0.91, 0.92, 0.93, 0.94, 0.95, 0.96, 0.97, 0.98, 0.99, or more. In some embodiments, the best enrichment parameters result in a root square mean error for the linear best fit curve of about 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, or 0.55 or more.

Once a linear best fit curve has been established for a microorganism(s) in a sample lot, the linear best fit curve can be used to quantitate the amount of that microorganism(s) in a test sample on a CFU per mass and/or volume basis. Thus, some embodiments are directed to methods of quantifying microorganism concentration in a sample comprising: (a) collecting a test sample from a test sample lot; (b) incubating the test sample (i) in a quantification medium (ii) for a pre-determined quantification time, (iii) at a pre-determined dilution ratio, and (iv) at a pre-determined temperature, wherein (i)-(iv) correlate to a pre-determined linear best fit curve for the microorganism from the test sample lot; (c) detecting, if present, a target nucleic acid sequence of the microorganism in the test sample by a detection assay; and (d) comparing the results of the detection assay with the pre-determined linear best fit curve to quantify an amount of microorganism in the test sample.

For accuracy, the test conditions should align as close as possible with the conditions utilized to develop the linear best fit curve for a given microorganism(s) in a sample lot. Thus, a test sample is taken from a test sample lot that is of the type as the sample lot used in a method to establish a linear best fit curve. For example, if testing for *Salmonella* concentration in a chicken matrix, then a test sample is taken from a chicken matrix suspected of or known to comprise *Salmonella* and then utilized in a quantification assay under the same conditions that were previously utilized to develop a linear best fit curve for *Salmonella* in a chicken matrix. Thus, the incubation of the test sample will ideally take place in the same quantification medium as used to develop the linear best fit curve for a pre-determined quantification time that was utilized to develop the linear best fit curve, at a pre-determined dilution ratio of sample to medium utilized to develop the linear best fit curve, and at a pre-determined temperature utilized to develop the linear best fit curve. The quantification medium, the pre-determined quantification time, the pre-determined dilution ratio, and the pre-determined temperature are all determined from the methods of determining quantification conditions for a microorganism in a sample described above, and are based on microorganism type(s) and sample type.

In some embodiments, the methods of determining quantification conditions for a microorganism in a sample and the methods of quantifying microorganism concentration in a sample are combined into a single method, i.e., the quantification conditions are first determined and then a test sample lot is tested with using the linear best fit curve established conditions.

The present methods may be broadly applied to a sample from any product including pork, fruits and vegetables (e.g., spinach or lettuce), beef, poultry (e.g., chicken or turkey), fish and other seafood, game (e.g., sheep, bison, deer, or elk), juices, dairy products, eggs, dry goods (e.g., cereals, nuts, etc.), yogurt, herbs and spices, and any type of raw or processed foods. The sample may be liquid or solid, and can include beverages (e.g., water, milk, fruit juices).

In some embodiments, the quantification medium is a medium that will provide the best growth of the microorganism(s) to be detected in the shortest amount of time. Selective media for the microorganism(s) to be detected have been developed for a variety of microorganisms and one of skill in the art will know to select a medium appropriate for the particular microorganism(s) to be detected. A general discussion and recipes of non-selective media are described in the FDA Bacteriological Analytical Manual (1998) published and distributed by the Association of Analytical Chemists, Suite 400, 2200 Wilson Blvd, Arlington, Va. 22201-3301. For example, in some embodiments, BAX® MP medium (Hygiena, LLC, Camarillo, Calif.) is effective as a selective medium, e.g., when *Salmonella* is the microorganism to be detected. For embodiments where background flora is observed (and such flora does not need quantification), ingredients of the selective medium can be changed, supplemented, or eliminated to optimize growth of the microorganism to be detected while preventing growth of background flora.

EXAMPLES

General Methods and Materials Used in the Examples

Materials and methods suitable for the maintenance and growth of bacterial cultures are well known in the art. Techniques suitable for use in the following Examples may be found in Manual of Methods for Genus Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in Biotechnology: A Textbook of Industrial Microbiology, Second Edition (1989) Sinauer Associates, Inc., Sunderland, Mass. or Bacteriological Analytical Manual. 6th Edition, Association of Official Analytical Chemists, Arlington, Va. (1984).

All PCR reactions are carried out using a standard BAX® System (Hygiena, LLC, Camarillo, Calif.). Briefly, samples are enriched, and a rack file with data on each sample is created. 150 μL of protease is added to 12 μL lysis buffer to create a lysis reagent. Add 200 μL lysis reagent to cluster tubes, and transfer enriched samples (e.g., 20 μL *E. coli*, 5 μL *Salmonella*, 5 μL *Listeria*) to the cluster tubes. Heat cluster tubes (first stage) in a thermal block (e.g., 37° C. for 20 minutes for *Campylobacter, E. coli, Salmonella, Shigella*, or *Vibrio;* 55° C. for 60 minutes for *Staphylococcus aureus;* 55° C. for 30 minutes for *Listeria*). Heat cluster tubes (second stage) in a thermal block at 95° C. for 10 minutes (all targets). Cool cluster tubes 5 minutes in a cooling block. Initialize cycler/detector. Arrange PCR tube in PCR cooling block. Hydrate PCR tablets with 30 μL lysate from cooled cluster tubes (for *Salmonella*, let PCR tubes with lysate sit in the cooling block for 10-30 minutes before loading samples into the BAX® System instrument). Place PCR tubes in cycler and run desired program. Review results on display screen.

The meaning of abbreviations is as follows: "h" means hour(s), "min" means minute(s), "sec" means second(s), "d"

means day(s), "ml" means milliliter(s), "µl" means microliter(s), "CFU" means colony forming unit(s), "CT" means cycle threshold.

Example 1

A single colony of *Salmonella* Enteriditis, *Salmonella* Typhimurium, and *Salmonella* Heidelberg were each suspended into 8 mL of BHI broth and incubated at 35° C. overnight. The next day, a 3-strain cocktail was created by removing 1 mL from each culture into a single tube. This cocktail was serially diluted in additional BHI broth and plated onto BHI agar to determine the CFU/mL.

Sufficient quantities of four poultry rinsates were divided into 11 contamination levels for each matrix type (parts, re-hang, post chill and staged): 0 to 5 $\text{Log}_{10}$ CFU/mL of rinsate in 0.5 $\text{Log}_{10}$ CFU/mL increments:

| $\text{Log}_{10}$ Inoculation | CFU/mL - Targeted | CFU/sample - Targeted | CFU/sample - Actual |
|---|---|---|---|
| 0 | 1 | 30 | 30.7 |
| 0.5 | 3 | 90 | 91.26 |
| 1 | 10 | 300 | 307.3 |
| 1.5 | 32 | 960 | 975 |
| 2 | 100 | 3,000 | 3,073.2 |
| 2.5 | 320 | 9,600 | 9,750 |
| 3 | 1,000 | 30,000 | 30,498 |
| 3.5 | 3,200 | 96,000 | 97,500 |
| 4 | 10,000 | 300,000 | 304,980 |
| 4.5 | 32,000 | 960,000 | 975,000 |
| 5 | 100,000 | 3,000,000 | 3,049,800 |

Samples were divided into 30 mL test portions and spiked with appropriate volume to reach target level. Immediately after inoculation, each sample was enriched in 30 mL of prewarmed (42° C.) BAX MP media, hand mixed to homogenize and incubated at 42° C. for 4-10 hours. Sample aliquots were removed at 4, 6, 8, and 10 hours and tested by the BAX® System method in quintuplet according to the lysis procedure described below.

For each sample, 5 µL of enrichment was added to 200 µL prepared lysis reagent (150 µL of protease to one 12 mL bottle of lysis buffer) in cluster tubes. Lysis was performed on the automated thermal block by heating tubes for 20 minutes at 37° C. and 10 minutes at 95° C., and then cooling tubes at 4° C. Thirty microliters of lysate was transferred to Real-Time *Salmonella* PCR tubes and held for 10 minutes. All PCR tubes were loaded into the BAX® System Q7 instrument, and a full process was run according to the procedure described in the BAX® System User Guide.

Figure 1:
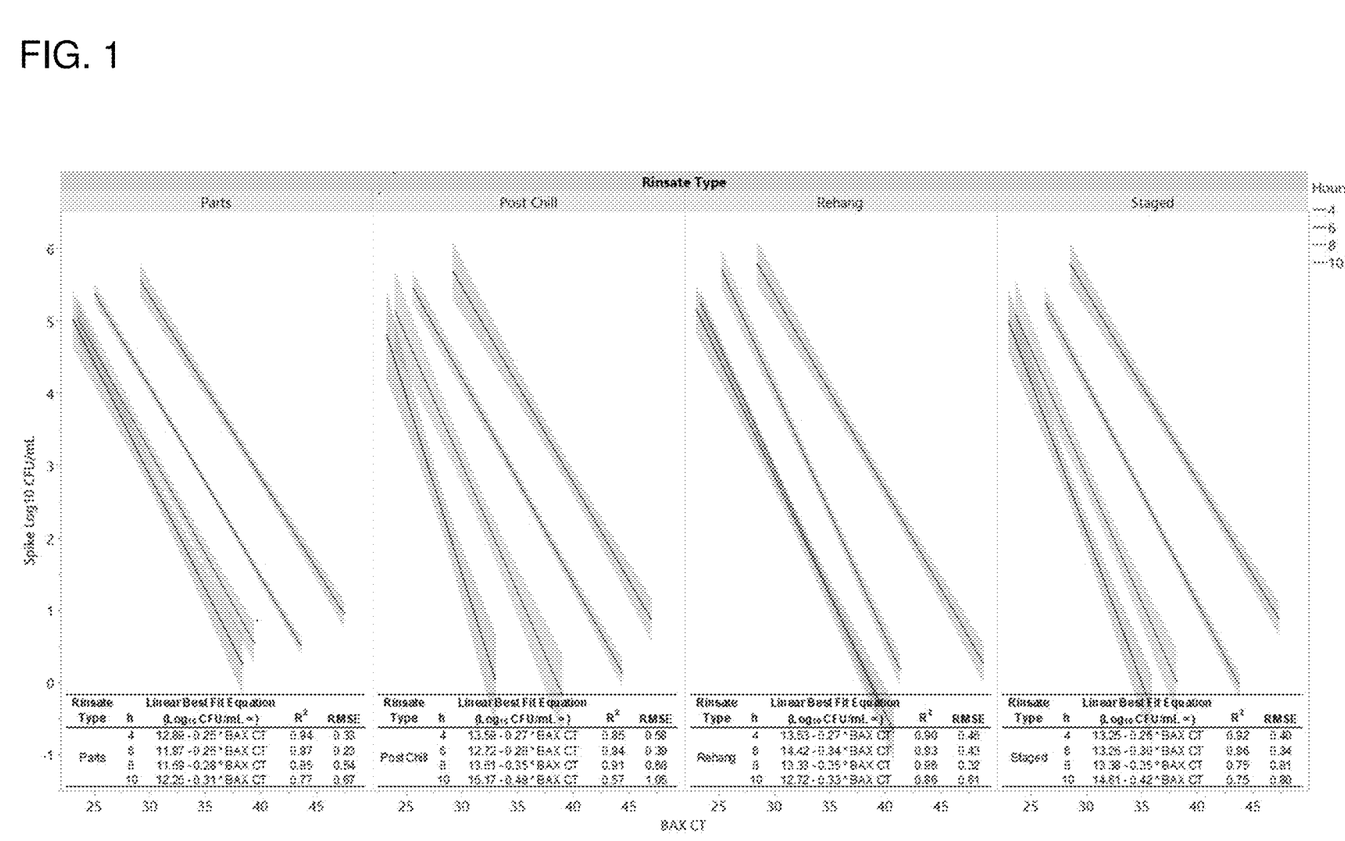
FIG. 1: Linear curves created to fit each rinsate type at each time point tested in Example 1.
Figure 2:
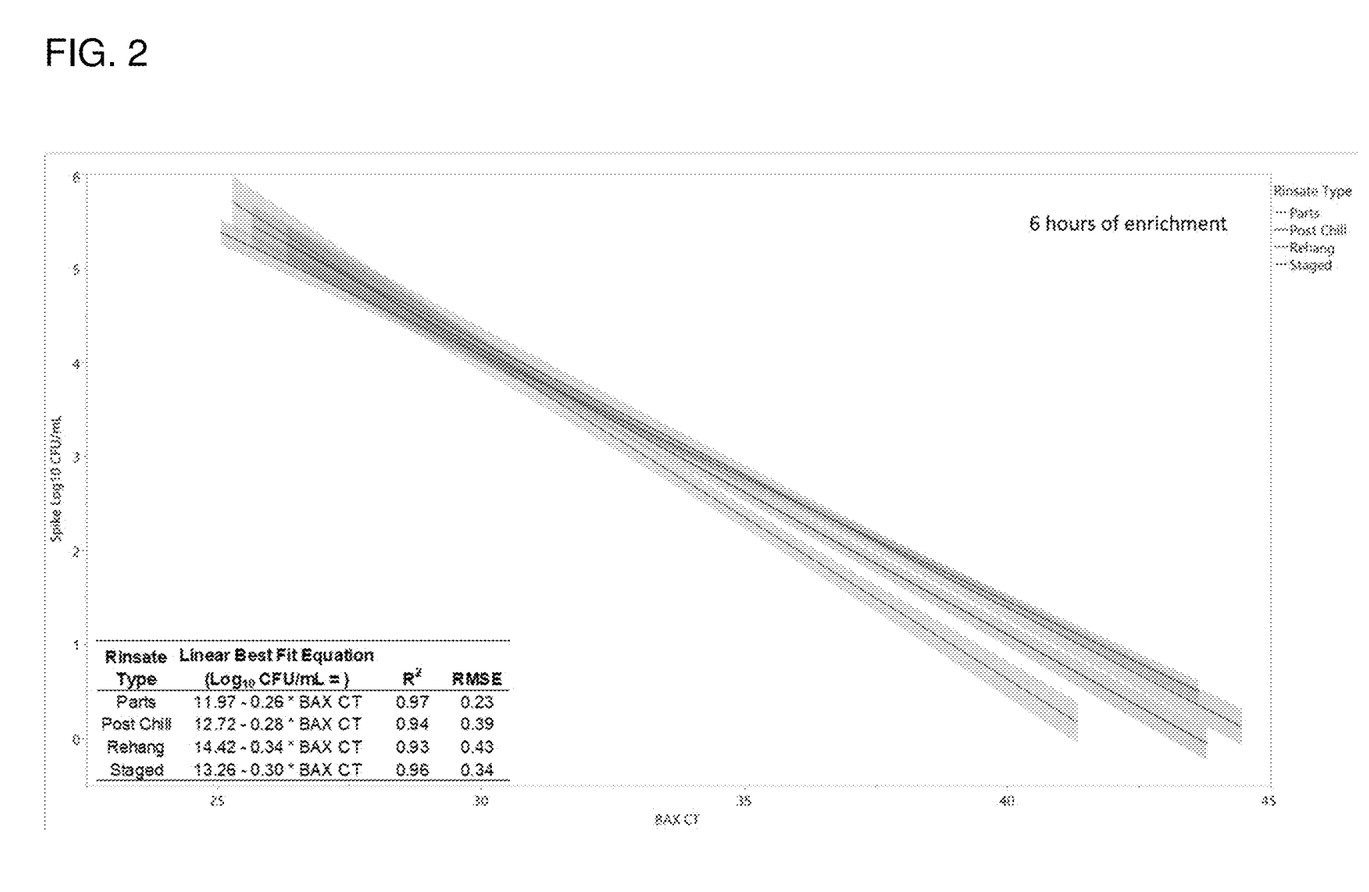
FIG. 2: Linear curve created to fit each rinsate type at 6 hours of enrichment in Example 1.

The obtained CT values at each timepoint and the inoculation levels were analyzed to create a linear fit equation to estimate $\text{Log}_{10}$ CFU/mL of *Salmonella* in all rinsate types. Linear curves were created for each rinsate type at 4, 6, 8 and 10 hours of enrichment. The linear curves at each time point were compared using $R^2$ and SE to determine the most appropriate enrichment time for all four rinsate types (FIG. 1). CT values captured after 6 hours of enrichment produced the best fit linear curve for all rinsate types (FIG. 2). This time point produced curves with an $R^2$ greater than 0.90, RMSE of less than 0.5 $\text{Log}_{10}$ CFU/mL and the SE at each inoculation level ranged from 0.04 to 0.26 $\text{Log}_{10}$ CFU/mL.

Utilization of BAX CT values for estimating $\text{Log}_{10}$ CFU/mL of *Salmonella*, in parts, re-hang, post chill and staged rinsates provides a wider enumerable range, decreased variation, reduced time to result, and less labor per sample compared to current industry standard MPN methodology.

Example 2 (Prophetic)

A single colony of *Salmonella* Enteriditis, *Salmonella* Typhimurium, and/or *Salmonella* Heidelberg is each suspended into approximately 8 mL of BHI broth and is incubated at 35° C. overnight. The next day, a 3-strain cocktail is created by removing 1 mL from each culture into a single tube. This cocktail is serially diluted in additional BHI broth and is plated onto BHI agar to determine the CFU/mL.

Sufficient quantities of two beef matrices are divided into three biological replications at 4-6 inoculation levels for each matrix type (beef trim and ground beef): 1 to 6 $\text{Log}_{10}$ CFU/mL of beef matrix in 1 $\text{Log}_{10}$ CFU/mL increments:

| $\text{Log}_{10}$ Inoculation | CFU/mL - Targeted | CFU/sample - Targeted |
|---|---|---|
| 1 | 10 | 300 |
| 2 | 100 | 3,000 |
| 3 | 1,000 | 30,000 |
| 4 | 10,000 | 300,000 |
| 5 | 100,000 | 3,000,000 |
| 6 | 1,000,000 | 30,000,000 |

Immediately after inoculation, each sample is enriched in prewarmed (42° C.) BAX MP media (375 g sample in 1.125 L medium), is hand mixed to homogenize and is incubated at 42° C. for 6-10 hours. Sample aliquots are removed at 6, 8, and 10 hours and are tested by the BAX® System method in quintuplet according to the lysis procedure described below.

Five technical replications are produced for each sample. For each technical replication, 5 µL of enrichment is added to 200 µL prepared lysis reagent (150 µL of protease to one 12 mL bottle of lysis buffer) in cluster tubes. Lysis is performed on the automated thermal block by heating tubes for 20 minutes at 37° C. and 10 minutes at 95° C., and then cooling tubes at 4° C. Thirty microliters of lysate is transferred to Real-Time *Salmonella* PCR tubes and held for 10 minutes. All PCR tubes are loaded into the BAX® System Q7 instrument, and a full process is run according to the procedure described in the BAX® System User Guide.

The obtained CT values at each timepoint and the inoculation levels are analyzed to create a linear fit equation to estimate $\text{Log}_{10}$ CFU/mL of *Salmonella* in all beef matrices. Linear curves are created for each beef matrix type at 6, 8 and 10 hours of enrichment. The linear curves at each timepoint are compared using $R^2$ and SE to determine the most appropriate enrichment time for both beef matrices. CT values that are captured after 6 hours of enrichment will produce the best fit linear curve for all beef matrices.

Example 3 (Prophetic)

A single colony of *Listeria monocytogenes* is suspended into approximately 8 mL of BHI broth and is incubated at 35° C. overnight. After overnight incubation, the strain is serially diluted in additional BHI broth and is plated onto BHI agar to determine the CFU/mL.

Sufficient quantities of five poultry rinsates are divided into three biological replications at 4-6 inoculation levels for each matrix type (parts, re-hang, post chill, staged, and ready-to-eat): 1 to 6 $\text{Log}_{10}$ CFU/mL of rinsate in 1 $\text{Log}_{10}$ CFU/mL increments:

| $Log_{10}$ Inoculation | CFU/mL - Targeted | CFU/sample - Targeted |
|---|---|---|
| 1 | 10 | 300 |
| 2 | 100 | 3,000 |
| 3 | 1,000 | 30,000 |
| 4 | 10,000 | 300,000 |
| 5 | 100,000 | 3,000,000 |
| 6 | 1,000,000 | 30,000,000 |

Immediately after inoculation, each sample is enriched in prewarmed (35° C.) BAX *Listeria* media (125 g sample in 375 mL medium), is hand mixed to homogenize and is incubated at 35° C. for 6-10 hours. Sample aliquots are removed at 6, 8, and 10 hours and are tested by the BAX® System method in quintuplet according to the lysis procedure described below.

Five technical replications are produced for each sample. For each technical replication, 5 µL of enrichment is added to 200 µL prepared lysis reagent (150 µL of protease to one 12 mL bottle of lysis buffer) in cluster tubes. Lysis is performed on the automated thermal block by heating tubes for 20 minutes at 37° C. and 10 minutes at 95° C., and then cooling tubes at 4° C. Thirty microliters of lysate is transferred to Real-Time *Listeria* PCR tubes and held for 10 minutes. All PCR tubes are loaded into the BAX® System Q7 instrument, and a full process is run according to the procedure described in the BAX® System User Guide.

The obtained CT values at each timepoint and the inoculation levels are analyzed to create a linear fit equation to estimate $Log_{10}$ CFU/mL of *Listeria* in all rinsate types. Linear curves are created for each rinsate type at 6, 8 and 10 hours of enrichment. The linear curves at each timepoint are compared using $R^2$ and SE to determine the most appropriate enrichment time for all five rinsate types. CT values that are captured after 6 hours of enrichment will produce the best fit linear curve for all rinsate types.

Example 4 (Prophetic)

A single colony of *Campylobacter jejuni* is suspended into approximately 8 mL of BHI broth and is incubated at 35° C. overnight. After overnight incubation, the strain is serially diluted in additional BHI broth and is plated onto BHI agar to determine the CFU/mL.

Sufficient quantities of five poultry rinsates are divided into three biological replications at 4-6 inoculation levels for each matrix type (parts, re-hang, post chill, staged, and ceca): 3 to 8 $Log_{10}$ CFU/mL of rinsate in 1 $Log_{10}$ CFU/mL increments:

| $Log_{10}$ Inoculation | CFU/mL - Targeted | CFU/sample - Targeted |
|---|---|---|
| 3 | 1,000 | 30,000 |
| 4 | 10,000 | 300,000 |
| 5 | 100,000 | 3,000,000 |
| 6 | 1,000,000 | 30,000,000 |
| 7 | 10,000,000 | 300,000,000 |
| 8 | 100,000,000 | 3,000,000,000 |

Immediately after inoculation, each sample is enriched in prewarmed (35° C.) BAX *Campylobacter* media (1 mL sample in 9 mL medium), is hand mixed to homogenize and is incubated at 35° C. for 6-10 hours. Sample aliquots are removed at 6, 8, and 10 hours and are tested by the BAX® System method in quintuplet according to the lysis procedure described below.

Five technical replications are produced for each sample. For each technical replication, 5 µL of enrichment is added to 200 µL prepared lysis reagent (150 µL of protease to one 12 mL bottle of lysis buffer) in cluster tubes. Lysis is performed on the automated thermal block by heating tubes for 20 minutes at 37° C. and 10 minutes at 95° C., and then cooling tubes at 4° C. Thirty microliters of lysate is transferred to Real-Time *Campylobacter* PCR tubes and held for 10 minutes. All PCR tubes are loaded into the BAX® System Q7 instrument, and a full process is run according to the procedure described in the BAX® System User Guide.

The obtained CT values at each timepoint and the inoculation levels are analyzed to create a linear fit equation to estimate $Log_{10}$ CFU/mL of *Campylobacter* in all rinsate types. Linear curves are created for each rinsate type at 6, 8 and 10 hours of enrichment. The linear curves at each timepoint are compared using $R^2$ and SE to determine the most appropriate enrichment time for all five rinsate types. CT values that are captured after 6 hours of enrichment will produce the best fit linear curve for all rinsate types.

What is claimed is:

1. A method of determining quantification conditions for a microorganism in a sample comprising:
   (a) inoculating a plurality of samples from a sample lot with logarithmic serial dilutions of a microorganism in a quantification medium;
   (b) incubating the plurality of samples at one or more temperatures for a time period sufficient to detect the microorganism in the plurality of samples by a detection assay;
   (c) removing aliquots of the plurality of samples at a plurality of time points and at one or more temperatures of the incubation;
   (d) detecting a target nucleic acid sequence of the microorganism in each aliquot by the detection assay; and
   (e) determining a detection value at each time point and inoculation level to produce a linear best fit curve for the microorganism in the sample lot.

2. The method of claim 1, wherein step (a) comprises at least two replications of each of the plurality of samples at logarithmic increments over a range of interest.

3. The method of claim 1, wherein step (c) comprises at least five aliquots of each of the plurality of samples at each of the plurality of time points.

4. The method of claim 1, wherein the microorganism is *Salmonella*.

5. The method of claim 1, wherein the sample lot is a food matrix.

6. The method of claim 1, wherein the detection assay is a real-time detection assay.

7. The method of claim 6, wherein the real-time detection assay is real-time PCR.

8. The method of claim 1, wherein the time period is about 10 hours or less.

9. The method of claim 1, wherein the sample lot is poultry-derived.

10. The method of claim 1, whereby the linear best curve fit is capable of providing an $R^2$ of at least about 0.85.

11. A method of quantifying microorganism concentration in a sample comprising:
   (a) collecting a test sample from a test sample lot;
   (b) incubating the test sample (i) in a quantification medium (ii) for a pre-determined quantification time, (iii) at a pre-determined dilution ratio, and (iv) at a pre-determined temperature, wherein (i)-(iv) correlate to a pre-determined linear best fit curve for the microorganism from the test sample lot;

(c) detecting presence or absence of a target nucleic acid sequence of the microorganism in the test sample by a detection assay; and
(d) comparing the results of the detection assay with the pre-determined linear best fit curve to quantify an amount of microorganism in the test sample.

12. The method of claim 11, wherein the microorganism is *Salmonella*.

13. The method of claim 11, wherein the test sample lot is poultry.

14. The method of claim 11, wherein the test sample is a food matrix.

15. The method of claim 11, wherein the detection assay is a real-time detection assay.

16. The method of claim 15, wherein the real-time detection assay is real-time PCR.

17. The method of claim 11, wherein the pre-determined linear best curve fit provides an $R^2$ of at least about 0.85.

18. A method of quantifying microorganism concentration in a sample comprising:
(a) inoculating a plurality of samples from a sample lot with logarithmic serial dilutions of a microorganism in a quantification medium;
(b) incubating the plurality of samples in the quantification medium at one or more temperatures for a time period sufficient to detect the microorganism in the plurality of samples by a detection assay;
(c) removing aliquots of the plurality of samples at a plurality of time points of the incubation;
(d) detecting a target nucleic acid sequence of the microorganism in each aliquots by the detection assay;
(e) determining a detection value at each time point and inoculation level to produce a linear best fit curve for the microorganism in the sample lot;
(f) collecting a test sample from a test sample lot, wherein the test sample is of the same type as the sample lot;
(g) incubating the test sample in the quantification medium (i) for a pre-determined quantification time, (ii) at a pre-determined dilution ratio, and (iii) at a pre-determined temperature, wherein (i)-(iii) correlate to the linear best fit curve for the microorganism in the sample lot;
(h) detecting presence or absence of a test target nucleic acid sequence of the microorganism in the test sample by the detection assay; and
(i) comparing the results of the detection assay of step (h) with the linear best fit curve to quantify an amount of microorganism in the test sample.

19. The method of claim 18, step (a) comprises at least two replications of each of the plurality of samples at logarithmic increments over a range of interest.

20. The method of claim 18, wherein step (c) comprises at least five aliquots of each of the plurality of samples at each of the plurality of time points.

21. The method of claim 18, wherein the microorganism is *Salmonella*.

22. The method of claim 18, wherein the sample lot is a food matrix and the test sample is the same food matrix as the sample lot.

23. The method of claim 18, wherein the detection assay is a real-time detection assay.

24. The method of claim 23, wherein the real-time detection assay is real-time PCR.

25. The method of claim 18, wherein the time period is about 10 hours or less.

26. The method of claim 18, wherein the sample lot is poultry-derived and the test sample is the same poultry species as the sample lot.

27. The method of claim 18, whereby the linear best curve fit is capable of providing an $R^2$ of at least about 0.85.

* * * * *